United States Patent [19]

Smoot et al.

[11] Patent Number: 4,657,655

[45] Date of Patent: Apr. 14, 1987

[54] FOTO/PHORESIS APPARATUS

[75] Inventors: Jeffrey B. Smoot, Wauwatosa; Richard K. Vitek, Brookfield; William R. Gette, Milwaukee; Thomas E. Prieto, Cedarburg, all of Wis.

[73] Assignee: Fotodyne, Inc., New Berlin, Wis.

[21] Appl. No.: 824,133

[22] Filed: Jan. 30, 1986

[51] Int. Cl.[4] .............................................. B01R 5/00
[52] U.S. Cl. .............................. 204/299 R; 204/182.3
[58] Field of Search .......................... 204/299 R, 182.3

[56] References Cited

U.S. PATENT DOCUMENTS

| 3,663,395 | 5/1972 | Strickler | 204/299 R |
|---|---|---|---|
| 3,764,512 | 10/1973 | Greenwood et al. | 204/299 R |
| 3,773,647 | 11/1973 | Mandle et al. | 204/299 R |
| 3,870,612 | 11/1975 | Flygare et al. | 204/299 R |
| 4,295,949 | 10/1981 | Fujiwara et al. | 204/299 R |
| 4,312,728 | 1/1982 | Kamachi | 204/299 R |
| 4,360,418 | 11/1982 | Golias | 204/299 R |
| 4,385,974 | 5/1983 | Shevitz | 204/299 R |
| 4,391,689 | 7/1983 | Golias | 204/299 R |
| 4,427,294 | 1/1984 | Nardo | 204/299 R |
| 4,534,647 | 8/1985 | Gross et al. | 204/299 R |

FOREIGN PATENT DOCUMENTS

| 56-122945 | 9/1981 | Japan | 204/299 R |
|---|---|---|---|
| 56-164940 | 12/1981 | Japan | 204/299 R |

Primary Examiner—Arthur P. Demers
Attorney, Agent, or Firm—Ronald E. Barry

[57] ABSTRACT

An apparatus for electrophoretically separating, visualizing and photographing DNA fragments in agarose gels, the apparatus including an electrophoresis chamber havng a platform and an electrode located on each side of the platform, a transilluminator having a UV light source, a frame defining a viewing opening over said light source, and a UV filtering cover for enclosing said viewing opening, a tray having movable gates for defining an enclosure for the agarose gell in one position and for locating the tray on the platform in the chamber in the other position, and a camera assembly adapted to be mounted on the frame in the transilluminator for providing 1:1 magnification photographs of the DNA fragment migration patterns.

18 Claims, 8 Drawing Figures

4,657,655

FOTO/PHORESIS APPARATUS

BACKGROUND OF THE INVENTION

The standard method for separating, identifying and purifying DNA fragments is electrophoresis through agarose gel. The technique is simple and rapid requiring only bands of DNA in agarose gel, stained with low concentrations of ethidium bromide. The DNA can then be detected by direct examination of the gel in ultraviolet light. The electrophoretic migration rate of the DNA through the agarose gel is dependent upon the molecular size of the DNA, the agarose concentration, conformation of the DNA and the electric field strength. The apparatus used to make this study generally includes a gel support member, an electrophoresis chamber, a transilluminator, a camera and a power source.

SUMMARY OF THE INVENTION

The apparatus, according to the present invention, includes unique features in each of the components of this system, which simplify the handling of the specimens and provides very accurate results. The transilluminator has been provided with a cover which allows visualization of ethidium bromide stained DNA samples on agarose gels without the risk of eye and skin damage from UV radiation. This has been achieved by using a cover made of a UV radiation blocking material which eliminates the necessity for protective equipment, such as face shields or eyeglasses. A glass frame is used to hold a purple filter glass centered over the UV light source. The filter glass blocks all light except that of a narrow band centered at 300 nm. The glass frame is designed to position both the gel support tray and the camera hood so that very accurate one-to-one photographs can be taken of the specimen. A safety interlock is also provided which allows energization of the UV light source only when the viewing cover is closed or the camera hood is located in the proper position on the glass frame. The gel support tray is provided with a unique gating system which is used both for retaining the agarose solution on the surface of the tray until solidification of the gel is complete, as well as locating the support tray in the electrophoresis chamber.

DESCRIPTION OF THE INVENTION

Figure 1:
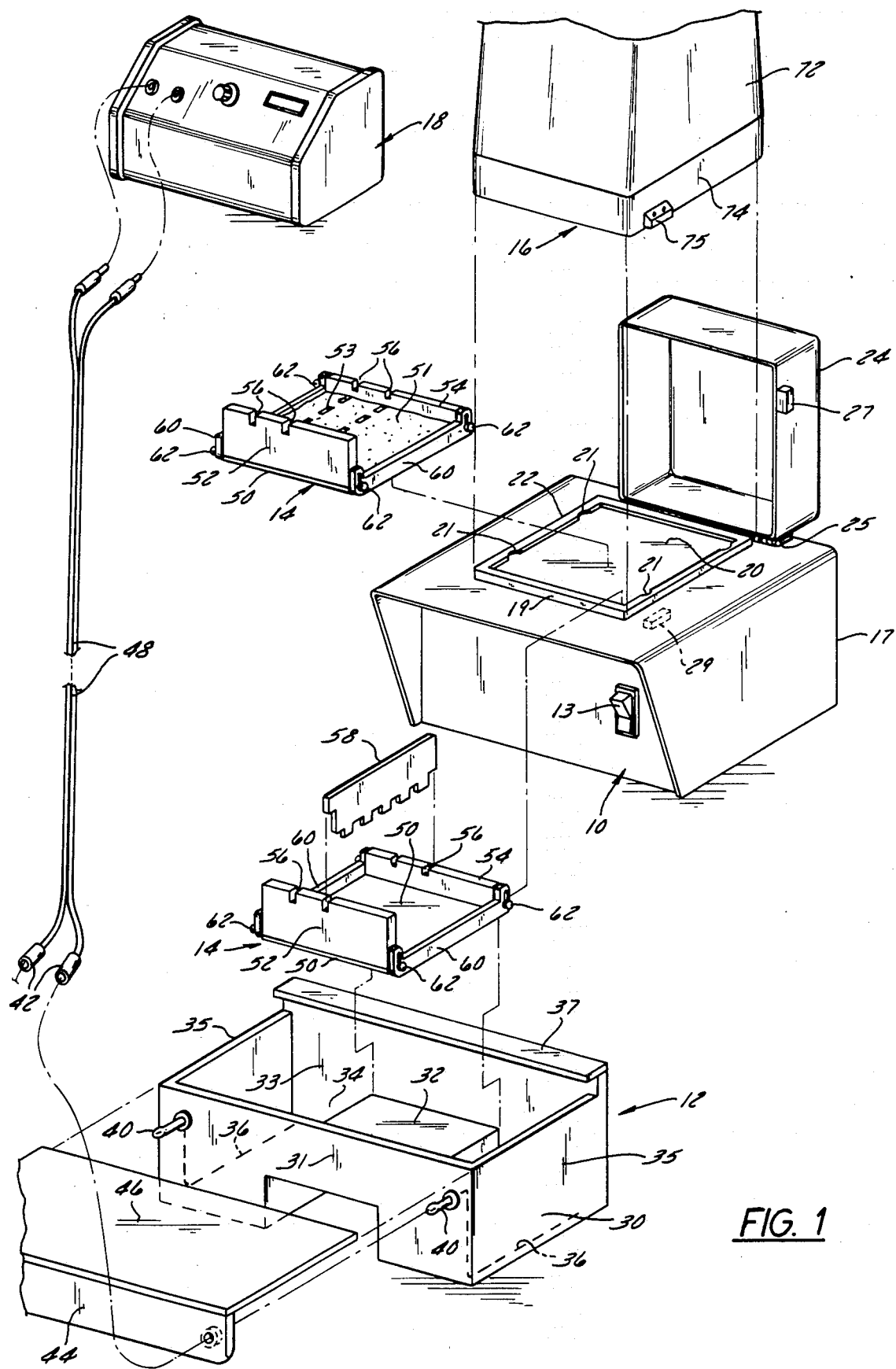
FIG. 1 is an exploded perspective view of the photo/foresis apparatus according to the invention.
Figure 2:
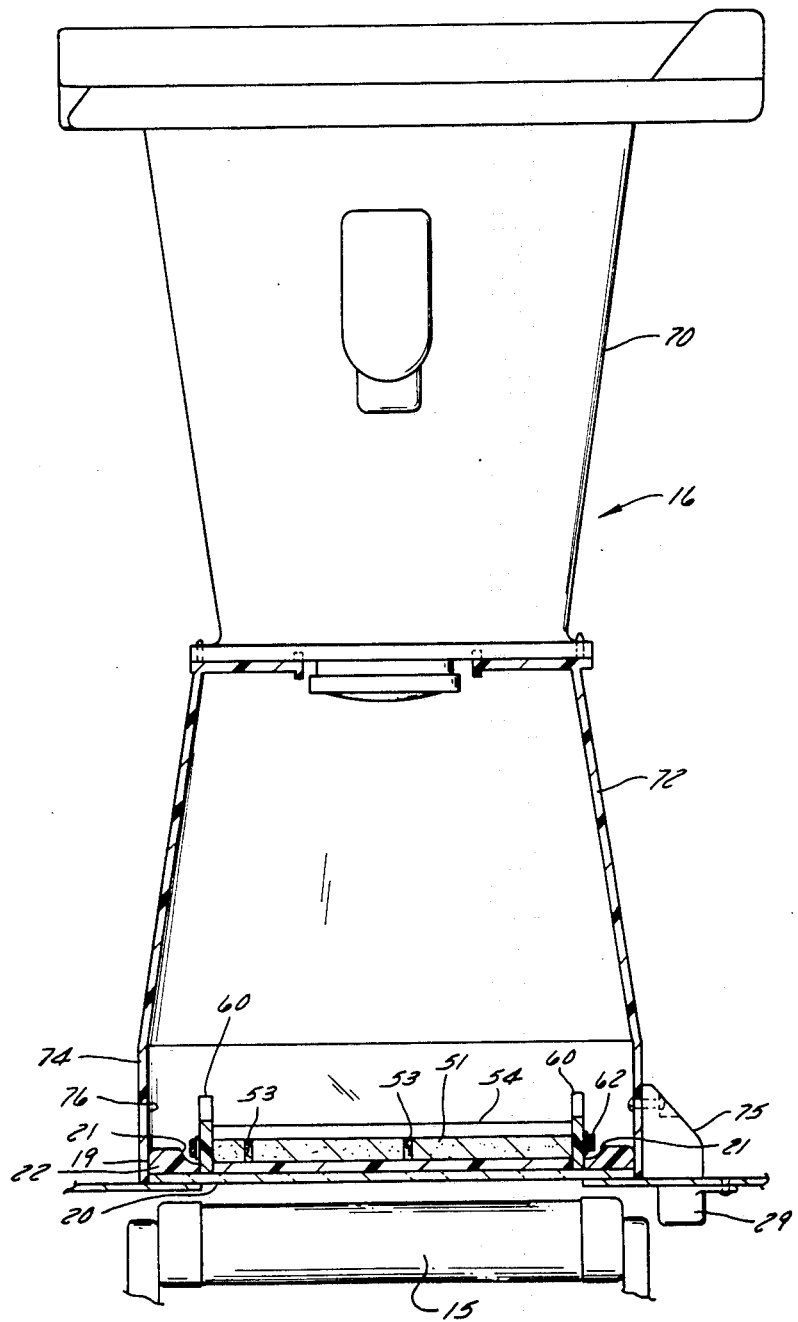
FIG. 2 is a side elevation view partly in section showing the camera assembly mounted on the transilluminator.
Figure 3:
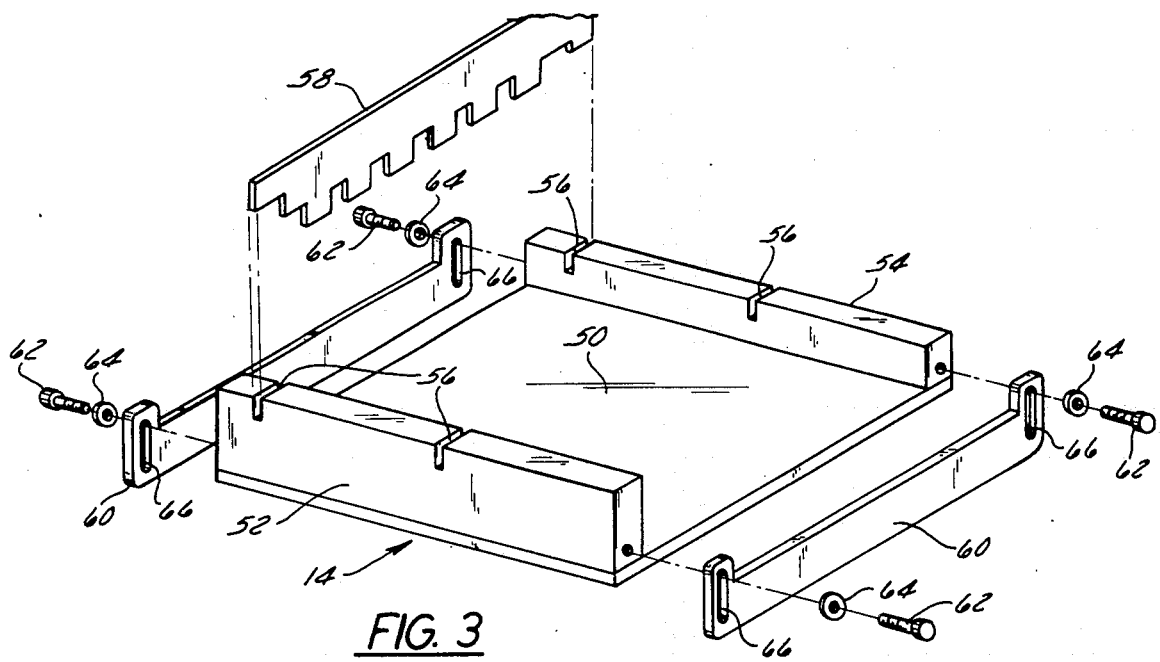
FIG. 3 is an exploded perspective view of the gel support tray.

The electrophoresis apparatus according to the present invention generally includes a transilluminator 10, an electrophoresis chamber 12, a gel support tray 14, a camera assembly 16, and a power source 18. The gel support tray 14 is provided with a unique gating system which allows the tray to be used to retain the agarose gel and to center the tray on the chamber 12. Transilluminator 10 is provided with a unique frame assembly which positively locates the tray 14 and the camera assembly 16 on the transilluminator 10.

Transilluminator

Figure 7:
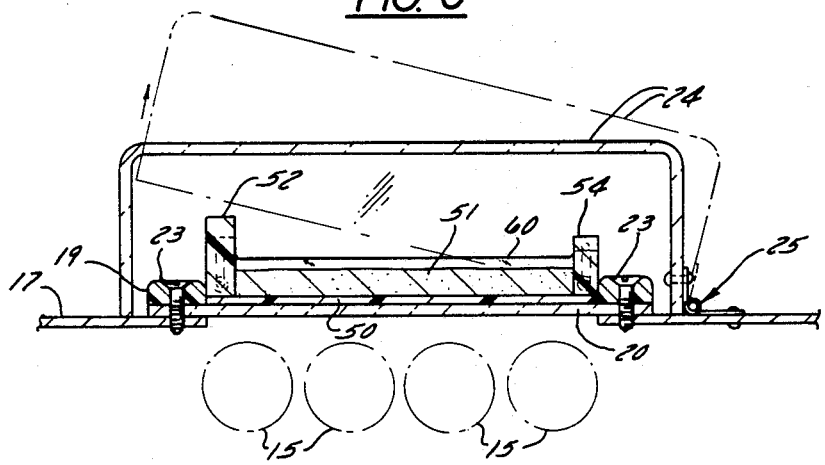
FIG. 7 is a side elevation section view of a portion of the transilluminator showing the gel support tray centered on the glass frame.
Figure 8:
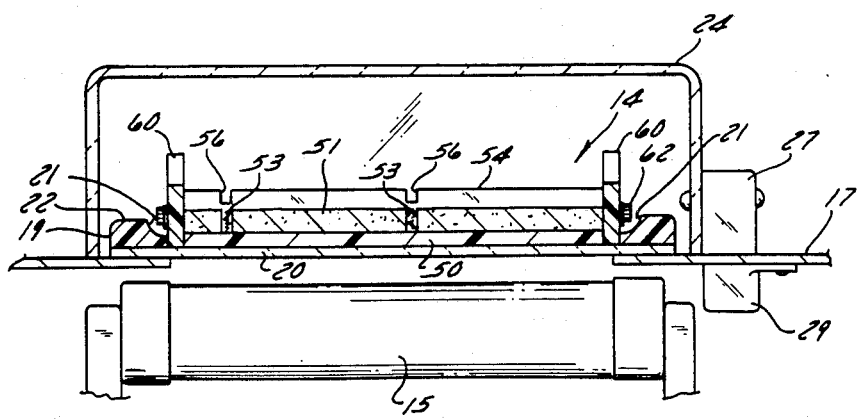
FIG. 8 is a front elevation section view of the portion of the transilluminator showing the support tray centered on the glass frame.

The transilluminator 10 basically is a high-intensity 300 nm UV light source with appropriate glass filtration to allow visualization of ethidium bromide stained DNA fragment patterns in agarose gel without the risk of eye and skin damage from UV radiation. A standard light source is provided in the transilluminator consisting of four 4-watt, 300 nm F4T5 fluorescent lamps 15 (FIGS. 7 and 8) located in the viewing area of the transilluminator 10. A manual switch 13 is provided on the front of the casing to energize the lamps. A cooling fan (not shown) is incorporated into the transilluminator 10 to prevent thermal damage to the DNA fragments agarose gel and other transilluminator components.

In accordance with the present invention, the transilluminator includes a casing or housing 17 having a purple filter glass 20 mounted on the top of the casing above the lamps 15 to block all light except that of a relatively narrow band centered at 300 nm. The filter glass 20 is held in place by a glass frame 22 which provides three unique features.

First, the glass frame 22 is provided with means in the form of the outer surface 19 which positions the camera 16 on the transilluminator 10 above the viewing area; second, the glass frame 22 includes means in the form of four indentations 21 which position the gel support tray 14 above the viewing area; and finally, the glass frame 22 is secured to the casing 17 by means of screws 23 which allow for easy replacement of the filter glass 20.

UV radiation protection is provided by means of a viewing cover 24 which is connected to a hinge 25 on the top of the casing 17 for the transilluminator 10. The viewing cover 24 is made of a material such as ultraviolet filtering acrylic plastic. Means are provided on the cover to prevent energization of the UV lamps 15 when the viewing cover is open. Such means is in the form of a magnet 27 on the front of the cover which cooperates with a magnetic safety interlock switch 29 located within the casing 17. The switch 29 is normally open and is connected in series with switch 13 to de-energize and to disable the power line for the lamps 15. When the magnet 27 on the cover is properly aligned with the switch 29, the switch will close to energize the lamps 15 if switch 13 is closed.

Electrophoresis Chamber

The electrophoresis chamber 12 generally includes a housing 30 having a front wall 31, a back wall 33 and side walls 35 and a tray support platform 32 centrally located in the housing. A lip 33 is provided on the top of back wall 33. A buffer well 34 is provided on each side of the platform 32. Platinum wire electrodes 36 are attached to the inside of the side walls 35 at the lower outer corners of each of the buffer wells 34. The electrodes 36 are connected to partially recessed banana plugs 40 located on the front wall of the chamber. The banana plugs 40 mate with recessed banana jacks 42 provided in the front wall 44 of a cover 46. The banana jacks 42 are connected to the power supply 18 by lead wire 48. The power supply 18 is a variable direct current power supply.

Gel Support Tray

The gel support tray 14 is used to provide both a preparation platform for the agarose gel 51 and a structural support for the gel to set up. The tray includes a plate 50 of UV transparent plastic with a front wall 52 and a back wall 54. Grooves 56 are provided in the front and back walls to position the well formers or combs 58. The tray is closed on the ends by means of gates 60 having a slot 66 at each end. The gates 60 are secured to the ends of the front wall 52 and back wall 54 by means of thumb screws 62 which pass through slots 66 and rubber "O" rings 64. The screws 62 are adjusted in the slots 66 so the pressure exerted by the "O" rings 64 allows for vertical movement of the gates but also holds the gates in the upper position. In the upper position, the gates 60 provide a holding area for the agarose gel 51 to set up. In the down position, the gates 60 provide a locating means for centering the tray on the platform 32 in the chamber 12. As is generally understood in the art, the combs 58 are used to form wells 53 in the gel 51 as the gel sets. After the gel sets the combs 58 are removed and DNA fragments placed in the wells.

Camera Assembly

Means are provided for documenting the DNA fragments in the gel which have been electrophoretically separated in the chamber 12 and illuminated on the transilluminator 10. Such means is in the form of the camera assembly 16, which includes an instant film camera 70 and a hood 72 having a fixed focal length. The hood is equipped with a diopter to produce a magnification of 1.0+or −3%. The hood 72 is provided with means in the form of an extension 74 opening at the outer end which has an inner peripheral surface 76 that conforms to the outer peripheral surface of the glass frame 22 provided on the transilluminator 10. When the hood extension is properly located on the glass frame 22, a photograph taken of the gel on the transilluminator 10 produces an exact image of the DNA fragment patterns in the gel.

Means are also provided on the hood for activating the switch 29 for the fluorescent lamps 15 in the transilluminator when the camera is properly placed on the frame. Such means is in the form of a magnet 75 located on the edge of the hood extension in a position to activate the magnetic switch 29 for the power system of the transilluminator.

Operation of the Apparatus

Figure 4:
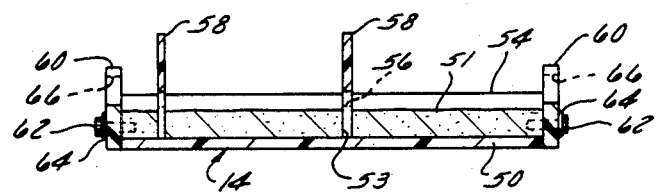
FIG. 4 is a side elevation view in section of the gel support tray.
Figure 5:
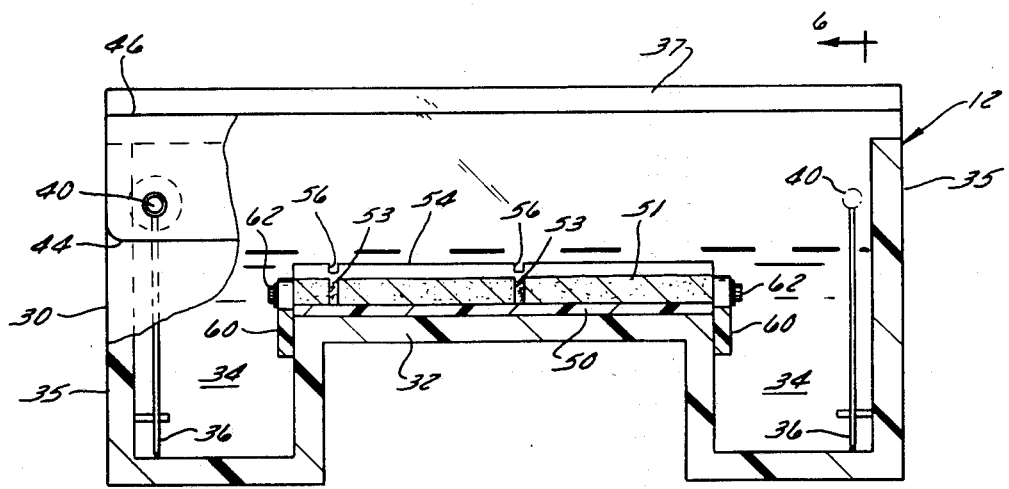
FIG. 5 is a side elevation view in section showing the support tray centered on the tray support platform in the chamber.
Figure 6:
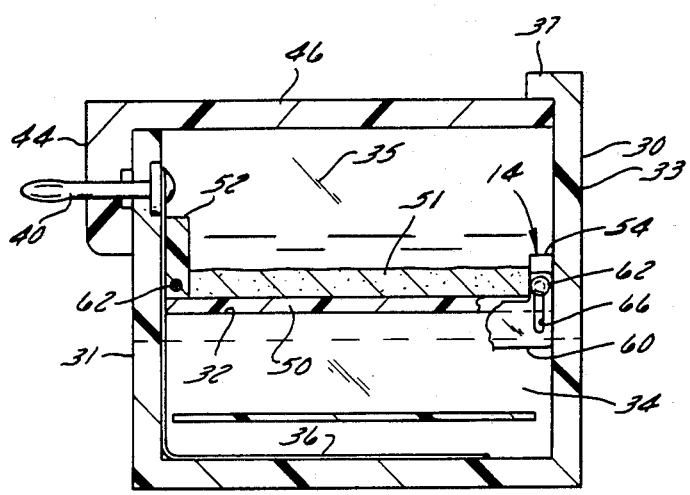
FIG. 6 is a view taken on Line 6—6 of FIG. 5 showing the support tray mounted on the platform in the chamber.

In operation the gates 60 on the tray 14 are set in the raised position (FIG. 4) and an agarose gel solution 51 is poured into the tray 14. Depending on the number of samples to be separated, one or two combs 58 can be positioned in the tray 14 to define the wells 53 for the DNA fragments. After the gel 51 has set, the combs 58 are removed from the gel. The tray 14 is then placed on the platform 32 in the chamber 12 with the gates 60 lowered so that the tray 14 is fixed in position on the platform 32. The buffer wells 34 are filled with a buffer such as tris-acetate, tris-phosphate, or tris-borate to a height sufficient to overflow the gel 51 and fill the wells 53. DNA fragments are then placed in wells 53 formed by the combs 58. The cover 46 is placed on the chamber and the power source 18 turned on to establish an electrical field between the electrodes 36.

The rate of migration of linear DNA fragments is proportional to the electric field strength and the time applied. After the desired separation has occurred, the power is turned off. The tray 14 is then removed from the platform 32 in the chamber 12. The gates 60 are raised and the tray 14 is then set in the glass frame 22 on the transilluminator 10. It should be noted that when placed in the glass frame 22, the thumb screws 62 will fit in the indentations 21 in the edges of the glass frame to positively locate the tray in an exact position within the glass frame 22. The manual switch 13 is turned on and the cover 24 is closed. When the magnet 27 closes the magnetic switch 29, the lamps will be energized and the ethidium bromide stained DNA fragments can be viewed through the UV filter cover 24.

If a picture is to be taken of the gel 51, the cover 24 is raised de-energizing the lamps. The camera 16 is placed on the transilluminator with the opening at the end of the camera hood 72 aligned with the outer periphery of the glass frame 22. When properly aligned, the magnet 75 on the hood will close the magnetic switch 29, energizing the lamps 15 in the transilluminator. The camera 70 can then be used to take an exact 1:1 picture of the DNA fragments in the gel.

The embodiments of the invention in which an exclusive property or privilege is claimed, are defined as follows:

1. An apparatus for separating and identifying DNA fragments in agarose gels comprising
   a tray having a front wall and a back wall,
   gate means mounted on each side of the tray for defining an enclosure within said walls for the agarose gel,
   means positioned in said tray for defining wells in the agarose gel for DNA fragments,
   an electrophoresis chamber having a platform and a buffer well on each side of the platform, said gate means being movable to positively locate the tray on said platform,
   means in said chamber for establishing an electric field across said tray,
   and means for illuminating said tray to visually observe the migration of said DNA fragments in the agarose gel.

2. The apparatus according to claim 1 wherein said illuminating means includes a normally open switch, a viewing cover mounted on said illuminating means for filtering UV radiation, and
   means on said cover for closing said switch when the cover is properly located on the transilluminator.

3. The apparatus according to claim 2 wherein said transilluminator includes a glass frame mounted on said transilluminator, said frame having an inner peripheral surface to positively locate the tray on the transilluminator.

4. The apparatus according to claims 1, 2 or 3 including a camera assembly having a fixed focal length for providing an exact image of said DNA fragments.

5. The combination of an electrophoretic chamber, a transilluminator and a tray for holding agarose gel containing DNA fragments, said chamber including a platform for supporting said tray and a well on each side of said platform for a buffer, said tray including means for forming an enclosure for said gel in one position and for positively locating the tray on the platform in the other position, means in said chamber for establishing an electrical field across said tray to effect a migration of said DNA fragments into the agarose gel, and said transilluminator including means for defining a viewing opening for illuminating said tray on said transilluminator.

6. The combination according to claim 5, including a camera assembly adopted to be mounted on said glass frame, said camera assembly including a hood having a fixed focal length for providing an exact picture of the DNA fragment migration patterns in said gel.

7. The combination according to claim 5 or 6, including a cover formed of a UV filter material mounted on said transilluminator in a position to enclose said viewing open defining means, whereby a tray placed in said viewing opening means can be observed without protective equipment.

8. The combination according to claim 7 wherein said transilluminator includes a normally open magnetically operated switch operatively connected to energize the transilluminator and said cover includes a magnetic member mounted on said cover for closing said switch when the cover is closed to energize said transilluminator.

9. The combination of an electrophoretic chamber, a transilluminator and a tray for holding agarose gel containing DNA fragments, said chamber including a platform for supporting said tray and a well on each side of said platform for a buffer, said tray including a front wall, a back wall and a gate on each side, said gates being movables between a first position for forming an enclosure for said gel, and a second position for positively locating the tray on the platform in said chamber, means in said chamber for establishing an electrical field across said tray to effect a migration of said DNA fragments into the agarose gel, and said transilluminator including a UV light source and a frame having an inner peripheral surface for defining a viewing opening for positively locating said tray over said light source in said transilluminator, and an outer peripheral surface.

10. The combination according to claim 9, including a camera assembly including a UV filter hood having an opening for engaging the outer peripheral surface of said glass frame, said hood having a fixed focal length for providing an exact picture of the DNA fragment migration pattern in said gel.

11. The combination according to claim 9 or 10, including a cover formed of a UV filter material mounted on said transilluminator in a position to enclose said viewing opening in said frame.

12. The combination according to claim 11 wherein said transilluminator includes a normally open magnetically operated switch mounted in said transilluminator and being connected to de-energize said transilluminator when said cover is open and said cover includes a magnet for closing said switch when the cover is closed.

13. A transilluminator for viewing a tray containing DNA fragment migration patterns in agarose gel, said transilluminator comprising a housing for a UV light source, and a cover formed of a UV filter material mounted on said housing in a position to cover said light source whereby a tray positioned over said light source can be viewed through said cover without protective glasses.

14. The transilluminator according to claim 13 including a frame for defining a viewing opening on said transilluminator and having an inner peripheral configuration corresponding to the outer configuration of said tray for locating said tray in said viewing opening.

15. The transilluminator according to claim 13 or 14 wherein said frame includes an outer peripheral surface corresponding to the inner peripheral surface of a camera hood for locating a camera over said viewing opening.

16. The transilluminator according to claims 12, 13 or 14 wherein said transilluminator includes a normally open magnetically operated switch mounted in said transilluminator and being connected to de-energize said transilluminator when the cover is open and said cover includes a magnet for closing said switch when the cover is closed.

17. The combination of an electrophoretic chamber and a tray for holding an agarose gel containing DNA fragments, said chamber having a platform for supporting said tray, a buffer well on each side of said platform and means for establishing an electric field across said platform, said tray including means for centering said tray on said platform.

18. The combination according to claim 17 wherein said centering means comprises a gate on each side of said tray mounted for movement between a first position for enclosing said tray and a second position for centering said tray on said platform.

* * * * *